United States Patent [19]
Adams et al.

[11] 3,988,473
[45] Oct. 26, 1976

[54] TERTIARY-ALKYLAMINO-LOWER ACYL-XYLIDIDE LOCAL ANAESTHETICS

[75] Inventors: Herbert J. F. Adams, Westboro, Mass.; Jon C. Anderson, Wyckoff, N.J.; Murray R. Blair, Jr., Sudbury, Mass.; Robert L. Di Rubio, Paxton, Mass.; Bertil H. Takman, Worcester, Mass.

[73] Assignee: Astra Pharmaceutical Products, Inc., Worcester, Mass.

[22] Filed: Mar. 24, 1975

[21] Appl. No.: 561,604

Related U.S. Application Data

[60] Division of Ser. No. 369,146, June 12, 1973, Pat. No. 3,925,469, which is a continuation-in-part of Ser. No. 325,378, Jan. 22, 1973, abandoned, which is a continuation-in-part of Ser. No. 230,114, Feb. 28, 1972, abandoned.

[52] U.S. Cl. .............................................. 424/324
[51] Int. Cl.² ..................................... A61K 31/165
[58] Field of Search ................................... 424/324

[56] References Cited
FOREIGN PATENTS OR APPLICATIONS

307,799  6/1955  Switzerland ........................ 260/562
771,151  3/1957  United Kingdom ................. 260/562

OTHER PUBLICATIONS

Epstein, et al., J. of Am. Pharm. Assn., 49, pp. 80–82 (1960).

Lofgren, et al., Acta. Chem. Scan. 11, pp. 1724–1737 (1957).

*Primary Examiner*—Jerome D. Goldberg
*Attorney, Agent, or Firm*—Brumbaugh, Graves, Donohue & Raymond

[57] ABSTRACT

Tertiary-alkylamino-lower acyl-xylidides have unusually long lasting local anaesthetic effect or high local anaesthetic activity while also having a satisfactory low level of tissue irritation and a satisfactory low acute toxicity. Combinations of such local anaesthetics with the biotoxins tetrodotoxin or saxitoxin are disclosed. Novel tertiary alkyl secondary amines, and methods for preparing such local anaesthetics and amines are also disclosed.

10 Claims, No Drawings

TERTIARY-ALKYLAMINO-LOWER ACYL-XYLIDIDE LOCAL ANAESTHETICS

This application is a division of co-pending application Ser. No. 369,146, filed June 12, 1973 (now U.S. Pat. No. 3,925,469), which latter application is a continuation-in-part of application Ser. No. 325,378, filed Jan. 22, 1973 (now abandoned), said application Ser. No. 325,378 being a continuation-in-part of application Ser. No. 230,114, filed Feb. 28, 1972 (now abandoned).

The present invention relates to tertiary-alkylamino-lower acyl-xylidide local anaesthetic compounds.

Two acylxylidide local anaesthetic compounds which are commercially available are N-n-butylpipecolyl-2,6-xylidide or bupivacaine sold under the trademark "Marcaine" having the structural formula

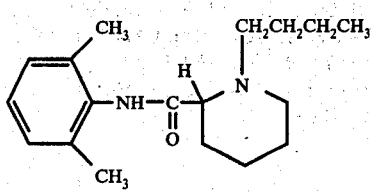

and diethylaminoaceto-2,6-xylidide or ω-diethylamino-2,6-dimethyl-acetanilide or lidocaine sold under the trademark "Xylocaine" having the structural formula

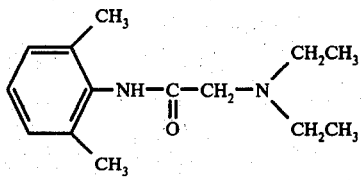

However, while bupivacaine or Marcaine is a long lasting local anaesthetic, it has the drawback of being more irritating to tissue than lidocaine and while lidocaine or Xylocaine is not irritating to tissue, it has the drawback of not being a long lasting local anesthetic.

Other local anaesthetics which are commercially available include α-propylaminopropiono-2-toluidide or prilocaine sold under the trademark "Citanest"; α-pyrrolidinoaceto-2,6-xylidide or pyrrocaine sold under the trademarks "Endocaine" and "Dynacaine"; and N-methylpipecolyl-2,6-xylidide or mepivacaine sold under the trademark "Carbocaine." However, these local anaesthetics are of short action.

It is, therefore, the principal object of the present invention to provide compounds which have an unusually long lasting local anaesthetic effect or high local anaesthetic activity while also having a satisfactory low level of tissue irritation and a satisfactory low acute toxicity.

The local anaesthetic compounds of the present invention are tertiary-alkylamino-acetoxylidides or -propionoxylidides. More specifically, these compounds are as follows:

A. 2-(tert.-butylamino)-2',6'-acetoxylidide

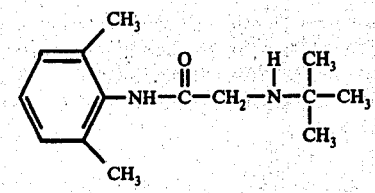

B. 2-(tert.-butylamino)-2',6'-propionoxylidide

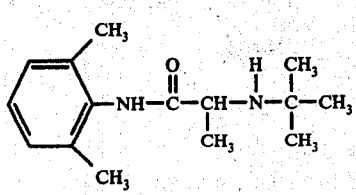

C. 2-(N-ethyl-tert.-amylamino)-2',6'acetoxylidide

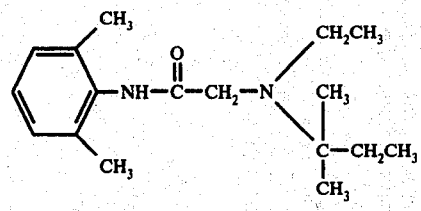

D. 2-(N-n-propyl-tert.-amylamino)-2',6'-acetoxylidide

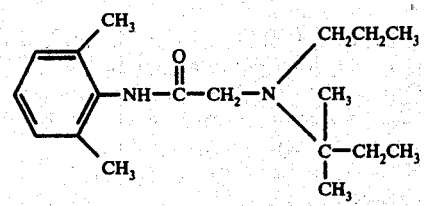

E. 2-(N-n-butyl-tert. butylamino)-2',6'-acetoxylidide

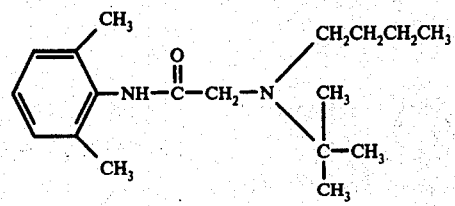

F. 2-(N-tert.-amylamino)-2',6'-acetoxylidide

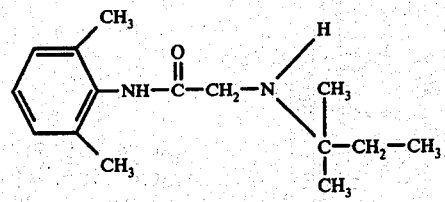

These compounds may be synthesized or prepared in accordance with the procedures given in the examples and illustrations set forth hereinafter.

These procedures or processes may be illustrated by

B. 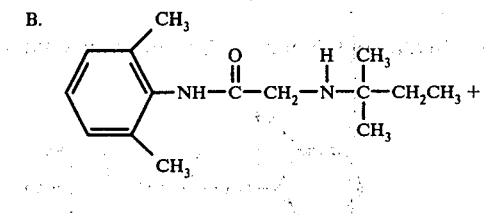 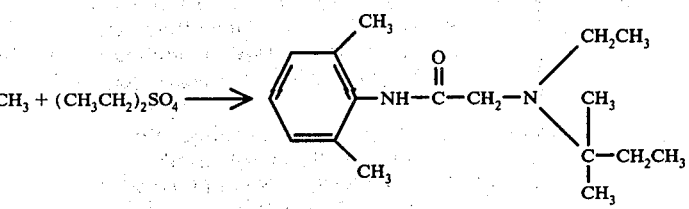

the following partial equations

IA. Preparation of 2-(tert.-butylamino)-2',6'-acetoxylidide.

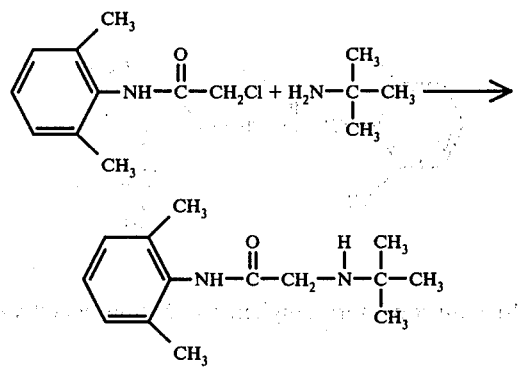

Instead of the chloro acetyl xylidide, the corresponding bromo- or iodo-compound may be used. If desired, NaI, KI or a suitably chosen quaternary ammonium iodide may be present during the reaction when the chloro- or bromo-compound is used.

IB. Preparation of 2-(tert.-butylamino)-2',6'-propionoxylidide.

This compound may be prepared by the procedure described in IA, using the corresponding 2-halo propionoxylidide, instead of the 2-halo acetoxylidide, as the starting material.

II. Preparation of 2-(N-ethyl-tert.-amylamino)-2',6'-acetoxylidide.

A. 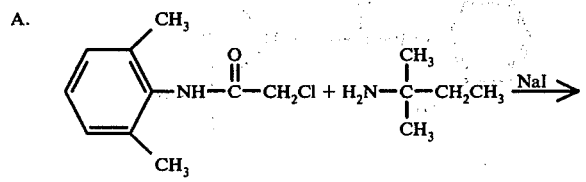

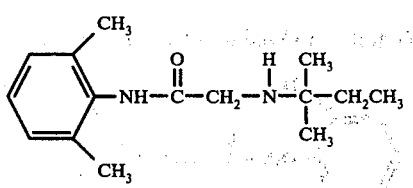

Instead of the chloro acetyl xylidide, the corresponding bromo-compound may be used. Also, instead of NaI, KI or a suitably chosen quaternary ammonium iodide may be used.

If, instead of the chloro or bromo acetyl xylidide, the iodo acetyl xylidide is used as the starting material, it will not be necessary to use the alkali metal iodide or quaternary iodide.

Instead of diethyl sulfate, other ethylating agents may be used, such as ethyl iodide or ethyl bromide.

The compounds may also be made by the reaction described below (III A), using $CH_3CHO$ as the starting material instead of $CH_3CH_2CHO$.

III. Preparation of 2-(N-n-propyl-tert.-amylamino)-2',6'-acetoxylidide.

A. 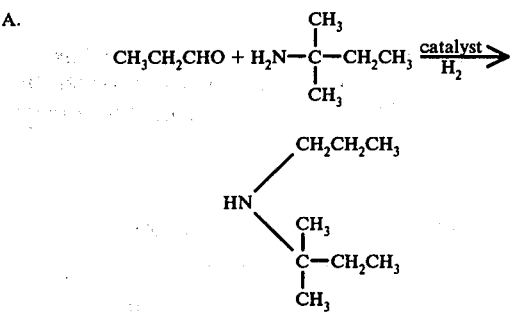

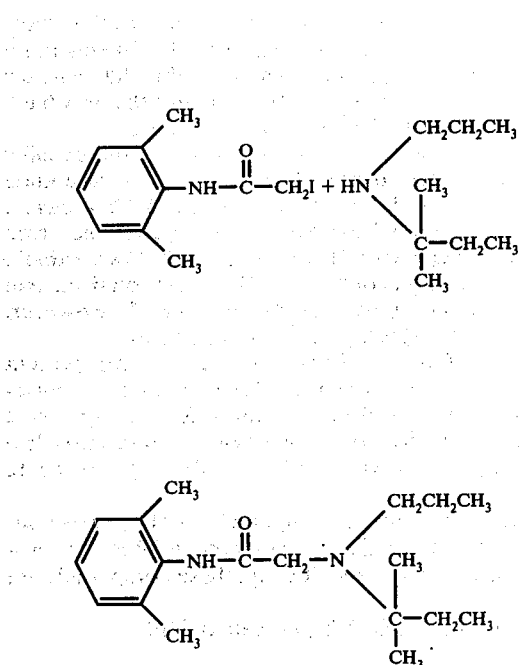

Instead of the iodo-acetyl xylidide, the corresponding chloro- or bromo-compound may be used as a starting material, in which case a suitable alkali metal or quaternary ammonium iodide will be used to promote the reaction, as in II above.

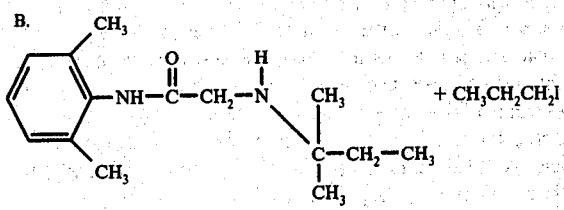

preferably with a suitable acid acceptor. Instead of n-propyl iodide, n-propyl bromide may be used.

Preparation of the sec. amines, N-ethyl-tert.-amyl amine, and N-n-propyl-tert.-amyl amine.

In addition to the methods described above, these compounds, which are intermediate compounds in the preparation of the local anaesthetic compounds of the invention, may be made as follows.

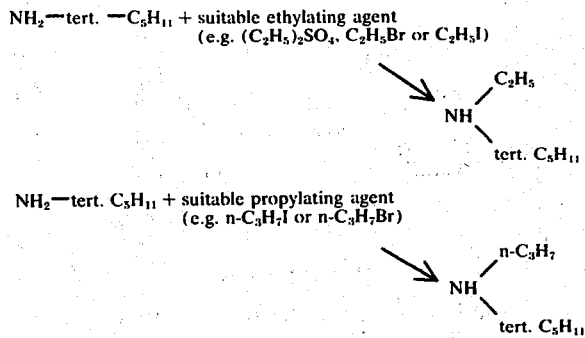

The compounds A, B, C and D of the invention above are useful as local anaesthetics in the conventional manner and employing conventional dosages thereof. The bases may be conventionally used in the form of solutions of their pharmaceutically acceptable salts, e.g., the hydrochlorides, tartrates and citrates. Anaesthetic compounds C and D above provide anaesthesia of significantly longer duration than compounds A and B. Compounds A and B could be used for short procedures in surgery, e.g., such as those requiring infiltration anaesthesia, minor nerve blocks, and certain forms of regional anaesthesia. Compounds C and D could be used in surgery when longer duration of anesthesia is desired. Because of the possibility of varying the concentration and dose of the agents it is however, possible to obtain satisfactory anaesthesia outside of the range exemplified above with both groups of agents. The compounds A, B, C, D, E and F, moreover when used in combination with the bioxtoxins tetrodotoxin or saxitoxin produce long lasting local anaesthetic effect.

The invention will be further illustrated by the following examples.

EXAMPLE 1

This example illustrates the preparation of 2-(tert.-butylamino)-2',6'-acetoxylidide. To 1 liter of absolute alcohol, 120 g. (0.608 mole) 2-chloro-2',60'-acetoxylidide and 272.2 g. (3.108 mole) tert.-butylamine were added. The reaction mixture was heated at 100° C. for 18 hours in an autoclave. After cooling the solvent was evaporated in vacuo. The cream colored residue was dried (vacuum desiccator) and then stirred in benzene for 30 minutes. The undissolved material (tert.-butylammonium chloride) was collected and discarded. The supernatant was evaporated in vacuo leaving a yellowish residue which was collected, dried, and recrystallized twice from petroleum ether (b.p.

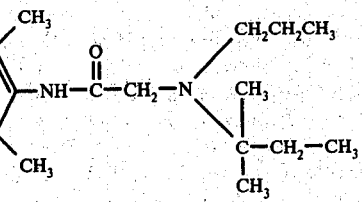

60°–110° C.). An 85.9% yield of a white crystalline material, m.p. 87°–88.5° C., was obtained.

Anal. Calcd. for $C_{14}H_{22}N_2O$: C, 71.75; H, 9.46. Found: C, 71.62; H, 9.43. Ir (KBr disc, base) 3318 (m; sec. amine, 3255 (m; amide, NH-stretch), 1673 (s; amide I), 1592 (w; aromatic), 1495 (s; amide II), 1385 (w) and 1370 (w) (methyl CH bending), 778 (s; 3 adjacent out of plane aromatic H) $cm^{-1}$.

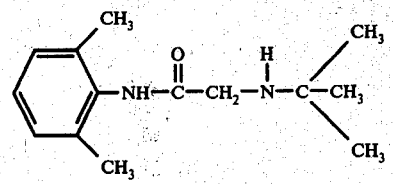

EXAMPLE 2

This example illustrates the preparation of 2-(tert.-amylamino)-2',6'-acetoxylidide, and the preparation of 2-(N-ethyl-tert.-amylamino)2',6'-acetoxylidide from 2-(tert.-amylamino)-2',6'-acetoxylidide.

2-(tert.-amylamino)-2',6'-acetoxylidide — To 400 ml. of anhydrous benzene, 18.9 g. (0.0956 mole) 2-chloro-2',6'-acetoxylidide, 20 g. (0.2295 mole) tert.-amylamine and 1 g. of sodium iodide were added. The reaction mixture was heated at 100° C. for 36 hours in an autoclave. A precipitate was collected and discarded. The resulting filtrate was stripped of solvent and the yellow oily residue was dissolved in ether, the undissolved material being collected and discarded. After drying ($Na_2SO_4$) the ether was stripped off in vacuo leaving a yellow oily liquid which was taken up in dilute hydrochloric acid (final pH 2). The acidic aqueous phase was washed several times with ether, basified to pH 9.5 with concentrated ammonia, and the precipitated base extracted with ether (4×100 ml.). The ether extract was dried ($Na_2SO_4$) and evaporated in vacuo leaving a yellow oily residue which was distilled in vacuo (b.p. 150° C., 0.05 mm.) to give under refrigeration, 16.6 g. of a white solid, m.p. 54°–55.5° C. (The hydrochloride was also prepared and recrystallized from acetonitrile, m.p. 209°–211° C.).

Anal. Calcd. for $C_{15}H_{24}N_2O$: C, 72.54; H, 9.74; N, 11.28. Found: C, 72.32; H, 9.98; N, 11.34. I.r. (KBr disc, hydrochloride) 3150(m-s; amide, NH stretch); 2710 (s), 2620 (m), 2580 (m), 2440 (m), and 2417 (m-w) ($NH^+$ stretch); 1665 (s; amide I), 1590 (m-w; aromatic), 1542 (s; amide II), 1393 and 1375 (s-m; methyl CH bending), 775 (s-m; 3 adjacent out of plane aromatic H) $cm^{-1}$.

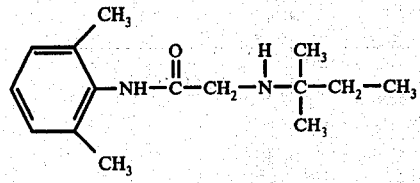

2-(N-ethyl-tert.-amylamino)-2',6'-acetoxylidide — To 46.52 g. (0.3017 mole) diethyl sulfate, 10.7 g. (0.0431 mole) 2-(tert.-amylamino)-2',6'-acetoxylidide was added, and the mixture was heated for 4 hours and 20 minutes at 100° C. After cooling the reaction mixture was taken up in hydrochloric acid (final pH 2). The mixture was washed with ether (2×100 ml.) and the aqueous solution basified to pH 9 with concentrated ammonia followed by extractions with ether (5×75 ml.). The combined ether extracts were dried ($Na_2SO_4$) and the ether removed in vacuo leaving a white solid residue. The residue was recrystallized three times from ethanol/$H_2O$. A 37.1% yield of a white crystalline material, m.p. 111.5°–113.5° C., was obtained.

Anal. Calcd. for $C_{17}H_{28}N_2O$: C, 73.87; H, 10.21; N, 10.14. Found: C, 73.94; H, 9.94; N, 10.21. I.r. (KBr disc, base) 3262 (s; amide, NH stretch), 1655 (s; amide I) 1590 (w; aromatic), 1498 (s; amide II), 1385 and 1375 (w; methyl CH bending), 766 (s; 3 adjacent out of plane aromatic H) cm$^{-1}$.

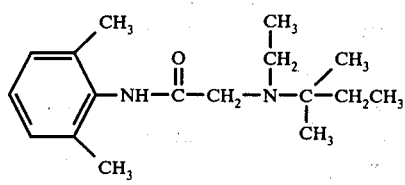

EXAMPLE 3

This example illustrates the preparation of 2-(N-n-propyl-tert.-amylamino)-2',6'-acetoxylidide from N-n-propyl-tert.-amylamine.

N-n-propyl-tert.-amylamine — A suspension of 1.0 g. of 10% palladium on charcoal in 100 ml. absolute alcohol was shaken with hydrogen until no more hydrogen was absorbed. To the catalyst mixture, 30 g. (0.3442 mole) tert.-amylamine was added followed by a solution of 18 g. (0.3098 mole) propionaldehyde in 50 ml. of absolute alcohol. All of the above ingredients were cooled in an ice bath before combining. After warming to room temperature, the reaction mixture was shaken with hydrogen at an initial pressure of 59 psi for 10 hours, by which time the theoretical amount of hydrogen was absorbed. The catalyst was separated by filtration, washed with ethanol, and 40 ml. of concentrated hydrochloric acid was added to the combined filtrate. The solution was brought to dryness by evaporation in vacuo. The dried product was dissolved in 250 ml. distilled water and 160 g. of 50% sodium hydroxide was added slowly with cooling to liberate the amine. The mixture was extracted with ether (3×200 ml.) and the combined ether extracts were dried over anhydrous sodium sulphate. The dried extract as distilled through a 300 mm. column packed with ⅛ inch ID glass helices yielding 26.7 g. (66.7%) on N-n-propyl-tert.-amylamine, b.p. 136.5°–137.5° C. (atmospheric pressure), $n^{22}_D$ 1.4106.

Anal. Calcd. for $C_8H_{19}N$: C, 74.34; H, 14.82; N, 10.84. Found: C, 74.76; H, 15.16; N, 10.96.

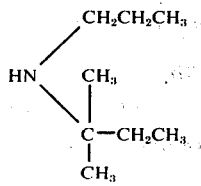

2-(N-n-propyl-tert.-amylamino)-2',6'-acetoxylidide — To 150 ml. benzene, 10 g. (0.0346 mole) 2-iodo-2',6'-acetoxylidide and 11.18 g. (0.0865 mole) N-n-propyl-tert.-amylamine were added. The reaction mixture was refluxed for 29 hours. After cooling the reaction mixture was stripped of benzene and unreacted amine in vacuo. The resulting semisolid material was treated with anhydrous ether. The undissolved material was filtered off and discarded and the ether was evaporated in vacuo. The yellow, waxy material was recrystallized twice from ethanol/water and twice from acetone/water. A 49% yield of a white crystalline material, m.p. 96.5°–97.5° C., was obtained.

Anal. Calcd. for $C_{18}H_{30}N_2O$: C, 74,43; H, 10.41; N, 9.65. Found: C, 74.4; H, 10.35; N, 9.59. I.r. (KBr disc, base) 3240 (m; amide NH stretch), 1665 (s; amide I), 1495 (s; amide II), 1385 and 1370 (w, methyl CH bending), 766 (s; 3 adjacent out of plane aromatic H) cm$^{-1}$. A hydrochloride was prepared from the base. It was obtained as a stable monohydrate melting at 181.2°–182.8° C.

Anal. Calcd. for $C_{18}H_{31}ClN_2O \cdot H_2O$: $H_2O$, 5.22; Found: (Karl Fischer) $H_2O$, 5.21.

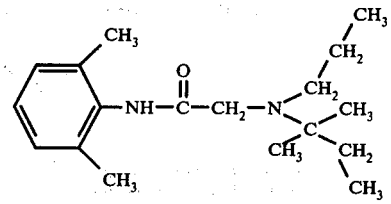

EXAMPLE 4

This example illustrates the preparation of 2-(tert.-butylamino)-2',6'-propionoxylidide To 300 ml. of absolute alcohol, 38.42 g. (0.15 mole) of 2-bromo-2',6'-propionoxylide and 54.85 g. (0.75 mole) of tertiary butylamine were added. The reaction mixture was heated at 100° C. for 18 hours in an autoclave. After cooling, the alcohol and unreacted amine were removed by distillation in vacuo. The residue was dissolved in ether and concentrated $NH_4OH$ was added. Undissolved material (tertiarybutylammonium bromide) was collected and discarded. The two phase supernatant was separated and the basic aqueous phase discarded. The ether phase was dried over anhydrous $Na_2SO_4$ and subsequently removed in vacuo. The cream colored residue was stirred in benzene for 30 minutes. Undissolved material (tertiarybutylammonium bromide) was collected and discarded. Evaporation of the benzene in vacuo gave a cream colored residue which was collected, dried and recrystallized three times from petroleum ether (b.p. 60°–110° C.). A 54.1% yield of a white crystalline material, m.p. 124.5°–126° C., was obtained.

Anal. Calcd. for: $C_{15}H_{24}N_2O$: Calcd.: C, 72.54; H, 9.74; N, 11.28; Found: C, 72,62; H, 9.83; N, 11.34

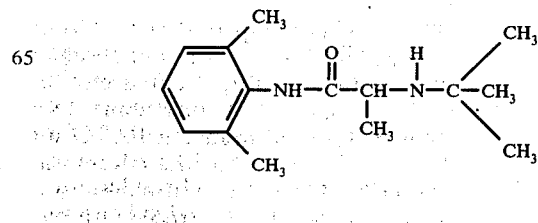

EXAMPLE 5

This example illustrates the preparation of N-n-propyl-tert. amylamine

A mixture of 2 moles of tert. amylamine and 1 mole of 1-brmo-propane is refluxed for 6 hours. The reaction mixture is cooled and kept at +4° C. for one hour. After filtering, the filtrate is fractionated by column distillation and the colorless, clear fraction boiling between 136°–138° C. is collected.

EXAMPLE 6

This example illustrates the preparation of 2-(N-ethyl-tert. amylamino)-2',6'-acetoxylidide A mixture of 0.170 mole of 2-(tert. amylamino)-2',6'-acetoxylidide (cf. Example 2), 0.187 mole of ethyl bromide, 0.085 mole of potassium carbonate and 300 ml of methyl ethyl ketone is refluxed with mechanical stirring for 36 hours. After evaporation of the low-boiling ingredients the residue is dissolved in dilute hydrochloric acid, is filtered and the acid solution is extracted twice with ether. The ether extract is discarded and the aqueous phase is made alkaline by the addition of concentrated ammonia to a pH of 9–10 whereafter it is extracted several times with ether. This ether extract is dried ($K_2CO_3$) and, after filtering, the ether is removed in vacuo. The residue is recrystallized from ethanol/water.

EXAMPLE 7

In a manner similar to the preparation of 2-(tert.-amylamino)-2',6'-acetoxylidide of Example 2, 2-chloro-2',6'-acetoxylidide is reacted with N-n-propyl-tert.-amylamine in the presence of sodium iodide to form 2-(N-n-propyl-tert. amylamino)-2',6'-acetoxylidide. The resulting reaction mixture is worked up as described in Example 3 for this compound.

EXAMPLE 8

This example illustrates the preparation of 2-[N-(n-butyl)-tert.-butylamino]-2',6'-acetoxylidide A mixture of 600 g. of 2-iodo-2',6'-acetoxylidide, 643 g. N-(n-butyl)-tert.-butylamine, and 4.5 liter of benzene were heated to reflux in a flask equipped with a mechanical stirrer and a reflux condenser for 15–16 hours. The compound N-(n-butyl)-tert.-butylamine is described by J. N. Tilley and A. A. R. Sayigh in J. Org. Chem. 28, 2076 (1963). It is prepared analogously to N-propyl-tert.-amylamine of Example 3 from n-butyraldehyde and tert.-butylamine. After cooling the precipitate of N-(n-butyl)-tert.-butylammonium iodide was filtered off (dry weight 482 g.). The filtrate was extracted with 4 M hydrochloric acid. (The acid extract can be filtered and washed with ether at this point). The acid extract was made alkaline with 7 M sodium hydroxide. The precipitate was taken up in methylene chloride and the alkaline solution was extracted with the same solvent. The methylene chloride solutions (combined) were dried ($Na_2SO_4$), after filtered, and evaporated. The residue was recrystallized from a mixture of acetone and water (7–8:1) and a yield of 414 g. was obtained, m.p. 140°–140.5° Calcd. for $C_{18}H_{30}N_2O$: C: 74.4, H: 10.4, N: 9.5. Found: C: 74.6, H: 10.5, N: 9.49.

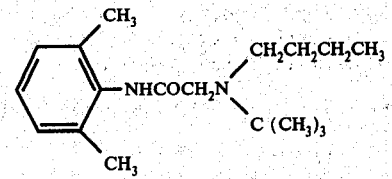

The compound 2-[N-(n-butyl)-tert.-butylamino]-2',6'-acetoxylidide may also be prepared by the procedure described in Example 6 from 2-(tert.-butylamino)-2',6'-acetoxylidide and n-butyl bromide.

It may also be prepared by the procedure described in Example 7 from 2-chloro-2',6'-acetoxylidide and N-n-butyl-tert.-butylamine.

In the tables presented below the following code designations have been used:

A is 2-(tert.-butylamino)-2',6'-acetoxylidide.
B is 2-(tert.-butylamino)-2',6'-propionoxylidide.
C is 2-(N-ethyl-tert.-amylamino)-2',6'-acetoxylidide.
D is 2-(N-n-propyl-tert.-amylamino)-2',6'-acetoxylidide.
E is 2-(N-n-butyl-tert.-butylamino)-2',6'-acetoxylide.
F is 2-(N-tert.-amylamino)-2',6'-acetoxylidide.
X is the prior art compound N-n-butylpipecolyl-2,6-xylidide, i.e., bupivacaine or Marcaine.
Y is the prior art compound diethylaminoaceto-2,6-xylide, i.e., lidocaine or Xylocaine.

Tables I, II and III contain comparative data on the duration of several of these local anaesthetic compounds, Table IV contains comparative data on the effect on the action potential of the isolated frog sciatic nerve preparation of some of these local anaesthetic compounds while Table V contains comparative data on the acute toxicity of several of these local anaesthetic compounds. Table VI contains the data from tests on peridural anaesthesia in the dog for compound D. Table VII contains data from tests run on compound B on rat sciatic nerve blocks, guinea pig wheals, irritation on the rabbit back, and acute toxicity in mice.

Irritation indices reported in Table VI are determined in the following manner.

Wheals are made on the shaved backs of albino rabbits by intradermal injection of aqueous solutions of the agents. Twenty-four hours later each wheal is graded for: presence and severity of erythema, presence and severity of edema, and presence or absence of necrotic tissue in the wheel. The grading is done on an arbitrary numerical scale, and a mean "irritation index" is calculated for all wheals at a given concentration.

TABLE I

| | Rat Sciatic Nerve Blocks* | | | | |
| | Duration in Minutes ± Standard Deviation | | | | |
| % Conc. as base | A | C | D | X | Y |
| --- | --- | --- | --- | --- | --- |
| 0.125 | 88 ± 11 | 115 ± 16 | 124 ± 50 | 121 ± 32 | — |

TABLE I-continued

Rat Sciatic Nerve Blocks*
Duration in Minutes ± Standard Deviation

| % Conc. as base | A | C | D | X | Y |
|---|---|---|---|---|---|
| 0.25 | 173 ± 20 | 159 ± 30 | 157 ± 30 | 175 ± 16 | 102 ± 15 |
| 0.5 | 184 ± 37 | 160 ± 10 | 217 ± 25*** | 212 ± 34 | 123 ± 10 |
| 1.0 | 250 ± 32 | 208 ± 35 | 8–27 days | 213 | 162 ± 39 |
| 2.0 | 276 ± 28** | 1–8 days | 13–30 days | — | 185 ± 23 |

All solutions contained 1:100,000 epinephrine.

*Test method given in Truant, A.P.: Arch Int. Pharmacodyn. 115: 483–497 (1958), which is incorporated by reference herein.
**Mean of 3; 7 blocked between 5 and 22 hours.
***Mean of 8; 2 blocked 10–13 days.

TABLE II

Guinea Pig Intradermal Wheals*
Duration in Minutes ± Standard Deviation

| % Conc. as base | A | C | D | X | Y |
|---|---|---|---|---|---|
| 0.25 | 129 ± 14 | 158 ± 49 | 171 ± 26 | 182 ± 4 | 78 ± 9 |
| 0.5 | 148 ± 20 | 230 ± 32 | 227 ± 21 | 252 ± 5 | 110 ± 13 |
| 1.0 | 186 ± 17 | 301 ± 11 | 253 ± 16 | 314 ± 10 | 117 ± 6 |
| 2.0 | 197 ± 14 | — | 303 ± 19 | — | 121 ± 12 |

All solutions contained 1:100,000 epinephrine.

*Test method given in Bulbring, E. and Wajda, I.: J. Pharmacol. Exp. Therap. 85: 78–84 (1945), which is incorporated by reference herein.

TABLE III

Peridural Anaesthesia in the Cat*
Duration of Block of Support of Weight in Minutes ± Standard Deviation

| % Conc. Base | A | C | X | Y |
|---|---|---|---|---|
| 0.5 | — | — | 136 ± 30 | — |
| 1.0 | 54 ± 9 | 220 ± 64 | 296 ± 77** | — |
| 2.0 | 104 ± 29 | 298 ± 56*** | — | 88 ± 10 |

All solutions contained 1:100,000 epinephrine.

*Test method given in Duce, B.R., Zelechowski, K., Camougis, G. and Smith, E.R.: Brit. J. Anaesth. 41: 579–587 (1969), which is incorporated by reference herein.
**Toxic effects observed at this concentration.
***Mean of 3 animals; 1 blocked > 7 hours.

TABLE IV

In vitro Studies on Frog Sciatic Nerve Block

| Compound | Conc. mM | Greatest Depth of Block (% of action potential) | Average time for 80% recovery of action potential - (min) |
|---|---|---|---|
| C | 20 | 77 | 29 |
| D | 5 | 96 | 163 |
| X | 5 | 64 | 65 |
| Y | 20 | 46 | 14 |

TABLE V

Acute Toxicity in Female Mice
LD$_{50}$ and 95% Fieller Confidence Limits: mg/kg as Base

| Compound | Intraperitoneal (I.P.) | Intravenous | Subcutaneous |
|---|---|---|---|
| A | 119(92–136) | 35.4(31.2–41) | 141(121–162) |
| C | 81(62–132) | 7.4(6.5–8.4) | — |
| D | 39(10–62) | 6.8(6.0–7.8) | 109(78–143) |
| X | 40(28–56) | 6.4(5.5–7.3) | 45(38–54) |
| Y | 105(93–132) | 19.5(18–24) | 211(183–256) |

Solutions did not contain epinephrine.

TABLE VI

Peridural Anaesthesia in the Dog*

Compound D

| Concentration (ml) | Volume (ml) | Duration (min) Digital Pain | Duration (min) Scrotal Pain |
|---|---|---|---|
| 1.0 | 10 | 289 (130–446) | 218 (192–251) |
| 2.0 | 5 | 338 (104–575) | 226 (110–445) |

Epinephrine 1:100,000 used in all solutions.
The values for the durations are mean values and the ranges are given in parentheses.

*Method: Mature male beagles are surgically prepared by implantation of a cannula into a lumbar vertebra so that drug solutions may be administered into the peridural space. After administration of local anaesthetic solutions, the animals are examined at intervals for duration of loss of pain in the scrotal area and in the digits of the hind limbs. Response to and awareness of pain stimuli in scrotal areas is a test for anaesthetic block in spinal roots L3–4 and S1–2–3. These roots are the furthest removed from the point of injection (L6) and, therefore, least likely to be affected by the anaesthetic. Return of response to pain in the scrotum is often the first sign of recovery and indicates recession of anaesthesia to at least L4 anteriorly and S2 posteriorly.

Table VII

Compound B: 2-(Tert.butylamino)-2', 6'-propionoxylidide
Local Anaesthetic and Actue Toxicity Testing

| Concentration % | Rat Sciatic* Duration Minutes | Frequency |
|---|---|---|
| .125% | 98 ± 7 | 8/10 |
| .25% | 106 ± 8 | 10/10 |
| .5% | 124 ± 5 | 10/10 |
| 1.0% | 144 ± 9 | 10/10 |
| 2.0%** | 164 ± 10 | 10/10 |

| Concentration % | Guinea Pig Wheal* Duration Minutes | Frequency |
|---|---|---|
| .25% | 139 ± 24 | 12/12 |
| .5% | 160 ± 43 | 12/12 |
| 1.0% | 184 ± 36 | 12/12 |

| Concentration % | Irritation Rabbit Back Irritation Index |
|---|---|
| .5% | 0 |
| 1.0% | 1.0 |
| 2.0% | .5 |

Acute Toxicity
LD$_{50}$ Mice
61 (45–78) mg/kg I.P.

*Solutions contained 1:100,000 epinephrine
**Depression, ataxia, loss of righting reflex in some animals at this concentration.

TABLE VIII

Formulations for 0.25%, 0.50%, 1.00%, 1.50%, and 2.00% Compound D:HCl solutions for injection containing 1:200,000 epinephrine are given below.

| | mg./ml. | | | | |
|---|---|---|---|---|---|
| | 0.25%* | 0.50% | 1.00% | 1.50% | 2.00% |
| Compound D:HCl H$_2$O | 2.64 | 5.28 | 10.55 | 15.82 | 21.10 |
| Sodium chloride, USP XVIII | 8.60 | 8.20 | 7.30 | 6.40 | 5.60 |
| Epinephrine, USP XVIII | 0.005 | 0.005 | 0.005 | 0.005 | 0.005 |
| Sodium metabisulfite | 0.50 | 0.50 | 0.50 | 0.50 | 0.50 |
| Water for injection, USP XVIII | | | qs ad 1.0 ml. | | |

*Indicates percent anhydrous Compound D:HCl

In Table IX data are presented showing the duration of blockage of rat sciatic nerves by compound E in concentrations of 0.25 – 1.0% w/v tested by the same method as used for the work reported in Table I. Frequencies and durations were good.

TABLE IX

Rat Sciatic Nerve Blocks
Compound E. Epinephrine 1:100,000.

| Concentration Per cent | Frequency | Duration (min.) Mean ± S.D. |
|---|---|---|
| 0.25 | 9/10 | 174 ± 26 |
| 0.5 | 10/10 | 200 ± 18 |
| 1.0 | 10/10 | 237 |

Test method: See Table I.

Compound E was also tested for toxicity in mice, rats, and guinea pigs. In mice the I.P. toxicity (LD$_{50}$) was 284 (218–531) mg/kg. In the rat, subcutaneous toxicity was 1068 (813–1507) mg/kg. In guinea pigs tested subcutaneously all animals survived 646 mg/kg.

The compounds of the present invention are also useful in combination with the known biotoxins, tetrodotoxin, desoxytetrodotoxin and saxitoxin as described and claimed in the copending application of Adams and Takman, Ser. No. 369,302 filed June 11, 1973, which is a continuation-in-part of application Ser. No. 206,181 filed Dec. 8, 171 (now abandoned) and in the copending application of Adams and Takman Ser. No. 369,147 filed June 12, 1973, which is a continuation-in-part of Ser. No. 206,182 filed Dec. 8, 1971 (now abandoned), the disclosures of which are incorporated herein by reference.

The following Table X gives the results of tests on the anaesthetic effect of various compositions of the aminoacylxylidides disclosed and claimed herein with the biotoxins, tetrodotoxin or saxitoxin. It will be noted that the herein claimed aminoacylxylidides have the distinct advantage, in combination with such biotoxins, of providing anaesthetics having usually long nerve-blocking effect.

Table X

Rat Sciatic Nerve Blocks* with Compounds A, B and F Added to the Biotoxins, Tetrodotoxin (TTX) or Saxitoxin (STX) Solutions. Concentration of TTX and STX 2 µg/ml.

| Compound | Biotoxin | Concn. of Compound (%) | Onset (min.) | Frequency | Duration |
|---|---|---|---|---|---|
| A | — | 0.5 | 5 | 5/5 | 126 ± 12 |
| A | — | 1.0 | 5 | 5/5 | 157 ± 18 |
| — | TTX | | 19 | 2/5 | 295** |
| A+ | TTX | 0.5 | 4 | 5/5 | >420 min.*** <24 hrs. |
| A+ | TTX | 1.0 | 3 | 5/5 | >420 min. <24 hrs. |
| B | — | 0.25 | 3 | 5/5 | 128 ± 13 |
| B | — | 0.5 | 2 | 5/5 | 133 ± 7 |
| — | TTX | | 19 | 4/5 | 316 ± 10** |
| B+ | TTX | 0.25 | 4 | 5/5 | >420 min. |
| B+ | TTX | 0.5 | 1 | 5/5 | >420 min. <24 hrs. |
| F | — | 0.5 | 3 | 6/6 | 97 ± 4 |
| F | — | 1.0 | 2 | 6/6 | 101 ± 8 |
| — | STX | | — | 0/6 | — |
| F+ | STX | 0.5 | 3 | 6/6 | >420 min. <24 hrs. |
| F+ | STX | 1.0 | 2 | 6/6 | >420 min. <24 hrs. |

*For test method, see Table I.
**One animal blocked >420 min.
***The notation >420 min. <24 hrs. means that the animals recovered during a period when they were not observed.
The test solution of compounds A and B contained epinephrine in a concentration 1:100,000.

The effect of compositions of compounds D and E, respectively, with tetrodotoxin (TTX) was also evaluated by tests on frog sciatic nerves. The pH of the tests was 5.6 and the method used is described below.

Compound D and TTX alone gave 24% and 29% reduction, respectively, in the action potential, whereas the combination of the two in the same concentrations reduced such potential by 94%. In the case of compound E, the reduction in the potential produced by the combination was 94%, as compared with 22% and 15%, respectively, for compounds E and TTX alone. There is, therefore, a decided advantage in the combination of the two drugs as compared with the individual compounds. (see Table XI).

TABLE XI

Effect of the presence of compounds D and E on Tetrodotoxin (TTX) blocks of isolated intact frog sciatic nerve at pH 5.6.

| Drug | Concentration | Percent reduction of the action potential | Number of experiments |
|---|---|---|---|
| D | 0.156 mM | 24(15–52)* | 8 |
| TTX | 3 · 10$^{-7}$M | 29(14–80**) | 6 |
| D + TTX | as above | 94(78–100) | 12 |
| E | 0.625 mM | 22(10–38) | 16 |
| TTX | 3 · 10$^{-7}$M | 15( 8– ) | 17 |
| E + TTX | as above | 94(80–100) | 17 |

*The numbers in parenthesis indicate the range observed in the experiments
**An occasional high value is sometimes observed. The logical explanation for this is some minute injury done to the nerve sheath during dissection. It takes about 50 times the concentration of TTX necessary to block a desheathed nerve in order to obtain the same degree of block of an intact (sheathed) nerve.

Following the procedure described above in Table VI, tests were made on the nerve blocking effect of compounds D and E, respectively, combined with the biotoxin, saxitoxin, in peridural anaesthesia in the dog.

The data obtained are presented below in Table XII. It will be noted that compound D alone gave a duration of block of digital pain and scrotal pain of 289 minutes and 218 minutes, respectively, whereas in combination with saxitoxin, duration of block was 1–2 days for digital pain and more than 8 hrs. for scrotal pain. Compound E in a 2% solution produced a duration of block of 1 to 2 days for digital pain and greater than 7½ hrs. for scrotal pain. All animals recovered completely.

TABLE XII

Peridural Anaesthesia in dog with compounds D and E added to Saxitoxin (STX) solutions. STX = 4 μg/ml. Volume 5 ml.

| Drug (concn.) | Duration of block of Digital Pain | Scrotal Pain |
|---|---|---|
| D 1% | 1–2 days | >480 min. <24 hrs. |
| E 2% | 1–2 days | >420 min. <24 hrs. |

Epinephrine 1:100,000 used in all solutions.
Method: See Table VI.
Note: A volume of 10 ml. 1% solution of Compound D gave durations of block of digital pain and scrotal pain of 289 min. and 218 minutes respectively (Table VI).

Compound D was also tested alone and in combination with saxitoxin (STX) in spinal anaesthesia in sheep. The results and the procedure followed are described in Table XIII below. It is significant that, particularly in the case of digital pain, the addition of compound D to saxitoxin increased the duration of block from about 69 to about 267, an increase of about 3½ fold.

TABLE XIII

Spinal Anaesthesia in Sheep with Compound D (0.25%) and Saxitoxin (STX) (3 μg/ml).

| Drug | Onset time (min.) | Duration of Block (Min.) Anal. Pain | Vulv.-Scrotal Pain | Digital Pain |
|---|---|---|---|---|
| STX | 3–8 | 172 | 95 | 69 |
| D + STX | 3 | 280 | 265 | 257 |

Method: The solutions contained 7.5% dextrose (pH 4.0). One ml. was administered in each experiment. The sheep (23–29 kg.) were restrained in the horizontal position during the injection and then immediately tilted so that the slope of the spine was positioned ten degrees to the horizontal plane (caudal inferior). The administration was performed between L6-S1 and was made with 22 gauge three inch disposable needles using the so-called "lateral" rather than the midline approach.
Note: Compound D alone in a concentration of 1%, i.e., four times the concentration used in the experiments summarized above, provided a duration of block of digital pain that lasted for 45–60 min. with an onset time of 5–10 minutes.

Compounds D and E were tested for their effect on the brain and the spinal cord in the peridural cat following the procedure described in Table III above. Compound D was tested in 1% concentration and compound E in 2% concentration. Following the tests the brain and the entire spinal cord were examined and no pathological change attributable to the drugs was found.

The results reported in the preceding tables on the in vitro studies on frog sciatic nerve were obtained by use of the following method, essentially as described by A. P. Truant, Arch. Int. Pharmacodyn. 115: 483–497 (1958):

Sciatic nerve trunks of *Rana pipiens* are prepared by dissecting the nerve from its roots in the spinal cord to the ankle and placing it on silver - silver chloride electrodes so that stimulation and recording can be performed during the course of application of the test compounds and during the recovery period. The bathing solution is Tasaki Ringer's, and for each block and recovery the pH's of the drug solution and the recovery solution were identical.

The irritation liability of the compound was determined according to a test procedure given in A. P. Truant, Arch. Int. Pharmacodyn. 115: 483–497 (1958). At the concentrations that are of clinical significance, compounds C and D were not more irritating than bupivacaine at 0.5% concentration.

The test method employed for the acute toxicity studies reported in Table V was as follows.

Sexually mature female animals are used.

Animals are divided into groups of 10 and dosed with drug solution or vehicle. After being dosed, animals are observed at intervals for several hours for overt effects and fatalities. Survivors are housed as groups according to dose level and checked once daily for the duration of the study in order to determine whether or not delayed fatalities occur.

$LD_{50}$'s and 95% Fieller confidence limits (or 95% approximate limits) are calculated by the Minimum Logit Chi Square Method of Berkson, J. Am. Stat. Assoc. 48: 565 (1953).

The tertiary-amylamino-acetoxylidide compounds of the invention (compounds C and D) have unusual, long-lasting local anaesthetic effect and high local anaesthetic activity, satisfactory low level of tissue irritation and satisfactory low acute toxicity compared with bupivacaine (compound X). The tertiary-butylamino-acetoxylidide compound of the invention (compound A) has an unusually long-lasting local anaesthetic effect and an unusually low intravenous toxicity compared to its structural isomer lidocaine (compound Y). Its tissue irritation liability is also quite satisfactory.

Generally, the compounds of the invention will be used in 0.25% – 2% water solution with or without addition of a vasoconstrictor in infiltration anaesthesia, peridural and subarachnoid anaesthesia. Their use is, however, not restricted to this concentration range and the dose and concentration used must be determined in each case with consideration given to such factors as the age and body weight of the patient, as well as to the route of administration, and the clinical anaesthetic requirements.

The compounds of the invention can also be applied topically to mucous membranes and damaged, e.g., abraided, skin in the form of solutions, ointments, jellies, or aerosols. Examples of suitable pharmaceutical compositions which may be used as local anaesthetics are given in Table VII, using compound D as the active ingredient. Similar compositions, using compounds A, B, C, E or F as the active ingredient may be formulated in a manner known in the art, possibly adjusting the NaCl content to obtain isotonicity.

We claim:

1. A pharmaceutical preparation which comprises, as an active ingredient, a local anesthetizing amount of a compound selected from the group consisting of 2-(N-ethyl-tert.-amylamino)-2′,6′-acetoxylidide, 2-(N-n-propyl-tert.-amylamino)-2′,6′-acetoxylidide, 2-(N-n-butyl-tert.-butylamino)-2′,6′-acetoxylidide, 2-(N-tert.-amylamino)-2′,6′-acetoxylidide and a pharmaceutically acceptable salt thereof, in association with a pharmaceutically acceptable carrier.

2. The pharmaceutical preparation defined by claim 1 wherein the compound is 2-(N-ethyl-tert.-amylamino)-2′,6′-acetoxylidide or a pharmaceutically acceptable salt thereof.

3. The pharmaceutical preparation defined by claim 1 wherein the compound is 2-(N-n-propyl-tert.-amylamino)-2',6'-acetoxylidide or a pharmaceutically acceptable salt thereof.

4. The pharmaceutical preparation defined by claim 1 wherein the compound is 2-(N-n-butyl-tert.-butylamino)-2',6'-acetoxylidide or a pharmaceutically acceptable salt thereof.

5. The pharmaceutical preparation defined by claim 1 wherein the compound is 2-(N-tert.-amylamino)-2',6'-acetoxylidide or a pharmaceutically acceptable salt thereof.

6. A method of inducing local anesthesia comprising locally administering to an animal a locally anesthetizing amount of a compound selected from the group consisting of 2-(N-ethyl-tert.-amylamino)-2',6'-acetoxylidide, 2-(N-n-propyl-tert.-amylamino)-2',6'-acetoxylidide, 2(N-n-butyl-tert.-butylamino)-2',6'-acetoxylidide, 2-(N-tert.-amylamino)-2',6'-acetoxylidide and a pharmaceutically acceptable salt thereof.

7. The method of inducing local anesthesia defined by claim 6 wherein the compound is 2-(N-ethyl-tert.-amylamino)-2',6'-acetoxylidide or a pharmaceutically acceptable salt thereof.

8. The method of inducing local anesthesia defined by claim 6 wherein the compound is 2-(N-n-propyl-tert.-amylamino)-2',6'-acetoxylidide or a pharmaceutically acceptable salt thereof.

9. The method of inducing local anesthesia defined by claim 6 wherein the compound is 2-(N-n-butyl-tert.-butylamino)-2,6'-acetoxylidide or a pharmaceutically acceptable salt thereof.

10. The method of inducing local anesthesia defined by claim 6 wherein the compound is 2-(n-tert.-amylamino)-2',6'-acetoxylidide or a pharmaceutically acceptable salt thereof.

* * * * *

UNITED STATES PATENT AND TRADEMARK OFFICE
CERTIFICATE OF CORRECTION

PATENT NO. : 3,988,473
DATED : October 26, 1976
INVENTOR(S) : Herbert J. F. Adams et al It is certified that error appears in the above-identified patent and that said Letters Patent are hereby corrected as shown below:

Col. 4, line 20, "compounds" should read -- compound --.
Col. 5, lines 66 and 67, "2-chloro-2',60'-acetoxylidide" should read -- 2-chloro-2',6'-acetoxylidide. Col. 6, line 59, "3150" should read -- 3150-3120 --. Col. 7, line 55, "as distilled" should read -- was distilled --. Col. 8, line 13, "49%" should read -- 49.4% --. Col. 9, line 6, "1-brmo-propane" should read -- 1-bromo-propane --. Col. 10, line 6, "N:9.5" should read -- N:9.65 --. Col. 12, line 31, under the caption "Concentration", "(ml)" should read -- (%) --. Col. 13, line 38, "June 11, 1973" should read -- June 12, 1973 --; line 40, "Dec. 8, 171" should read -- Dec. 8, 1971 --. Col. 16, line 50, "Table VII" should read -- Table VIII --.

Signed and Sealed this

Twenty-second Day of February 1977

[SEAL]

Attest:

RUTH C. MASON
Attesting Officer

C. MARSHALL DANN
Commissioner of Patents and Trademarks